(12) United States Patent
Hodges et al.

(10) Patent No.: US 11,413,443 B2
(45) Date of Patent: *Aug. 16, 2022

(54) ROTARY SEAL FOR CANTILEVERED ROTOR PUMP AND METHODS FOR AXIAL FLOW BLOOD PUMPING

(71) Applicant: TC1 LLC, St. Paul, MN (US)

(72) Inventors: William V. Hodges, Tracy, CA (US); Ian McEachern, Tracy, CA (US); Eric T. Lee, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/993,043

(22) Filed: Aug. 13, 2020

(65) Prior Publication Data

US 2021/0008262 A1    Jan. 14, 2021

Related U.S. Application Data

(63) Continuation of application No. 16/317,809, filed as application No. PCT/US2017/042858 on Jul. 19, 2017, now Pat. No. 10,857,273.

(Continued)

(51) Int. Cl.
*A61M 60/818* (2021.01)
*A61M 60/205* (2021.01)
(Continued)

(52) U.S. Cl.
CPC ........ *A61M 60/205* (2021.01); *A61M 60/148* (2021.01); *A61M 60/422* (2021.01); *A61M 60/818* (2021.01)

(58) Field of Classification Search
CPC .......................................... A61M 60/818–827
See application file for complete search history.

(56) References Cited

U.S. PATENT DOCUMENTS

| 2,712,792 | A | 7/1955 | Snyder |
| 4,082,376 | A | 4/1978 | Wehde et al. |

(Continued)

FOREIGN PATENT DOCUMENTS

| CA | 2624704 | 4/2007 |
| CN | 101282748 | 10/2008 |

(Continued)

*Primary Examiner* — George R Evanisko
(74) *Attorney, Agent, or Firm* — Kilpatrick Townsend & Stockton LLP

(57) ABSTRACT

Blood pump devices having improved rotary seals for sealing a bearing assembly supporting a rotor provided herein. Such rotary seals are particularly suited for use in blood pump devices that include rotors having cantilevered supported through a sealed mechanical bearing disposed outside a blood flow path of the device to avoid thrombus formation caused by blood contact with the bearing. The rotary seal can include a first and second face seal that are preloaded with a deflectable compliance member incorporated into the pump housing or a pair of magnets. Such rotary seals can instead or further utilize tight fitment between components or a bio-absorbable fill material to seal an interface between the rotor shaft and pump housing to seal the bearing assembly from fluid flowing through the pump.

19 Claims, 9 Drawing Sheets

Related U.S. Application Data

(60) Provisional application No. 62/365,305, filed on Jul. 21, 2016.

(51) Int. Cl.
*A61M 60/148* (2021.01)
*A61M 60/422* (2021.01)

(56) References Cited

U.S. PATENT DOCUMENTS

| | | | |
|---|---|---|---|
| 4,458,366 A | 7/1984 | MacGregor | |
| 4,508,535 A | 4/1985 | Joh et al. | |
| 4,625,712 A | 12/1986 | Wampler | |
| 4,643,641 A * | 2/1987 | Clausen | F16J 15/344 415/174.3 |
| 4,688,998 A | 8/1987 | Olsen et al. | |
| 4,704,121 A | 11/1987 | Moise | |
| 4,779,614 A | 10/1988 | Moise | |
| 4,817,586 A | 4/1989 | Wampler | |
| 4,846,152 A | 7/1989 | Wampler et al. | |
| 4,895,557 A | 1/1990 | Moise et al. | |
| 4,906,229 A | 3/1990 | Wampler | |
| 4,908,012 A | 3/1990 | Moise et al. | |
| 4,944,722 A | 7/1990 | Carriker et al. | |
| 4,957,504 A | 9/1990 | Chardack | |
| 4,994,078 A | 2/1991 | Jarvik | |
| 5,098,256 A | 3/1992 | Smith | |
| 5,106,273 A | 4/1992 | Lemarquand et al. | |
| 5,145,333 A | 9/1992 | Smith | |
| 5,376,114 A | 12/1994 | Jarvik | |
| 5,385,581 A | 1/1995 | Bramm et al. | |
| 5,393,207 A | 2/1995 | Maher et al. | |
| 5,405,251 A | 4/1995 | Sipin | |
| 5,441,535 A | 8/1995 | Takahashi et al. | |
| 5,443,503 A | 8/1995 | Yamane | |
| 5,588,812 A | 12/1996 | Taylor et al. | |
| 5,613,935 A | 3/1997 | Jarvik | |
| 5,695,471 A | 12/1997 | Wampler | |
| 5,707,218 A | 1/1998 | Maher et al. | |
| 5,711,753 A | 1/1998 | Pacella et al. | |
| 5,749,855 A | 5/1998 | Reitan | |
| 5,755,784 A | 5/1998 | Jarvik | |
| 5,824,070 A | 10/1998 | Jarvik | |
| 5,888,242 A | 3/1999 | Antaki et al. | |
| 5,904,646 A | 5/1999 | Jarvik | |
| 5,917,297 A | 6/1999 | Gerster et al. | |
| 5,928,131 A | 7/1999 | Prem | |
| 5,947,892 A | 9/1999 | Benkowski et al. | |
| 5,951,263 A | 9/1999 | Taylor et al. | |
| 5,957,672 A | 9/1999 | Aber | |
| 6,001,056 A | 12/1999 | Jassawalla et al. | |
| 6,018,208 A | 1/2000 | Maher et al. | |
| 6,050,975 A | 4/2000 | Poirier | |
| 6,066,086 A | 5/2000 | Antaki et al. | |
| 6,071,093 A | 6/2000 | Hart | |
| 6,093,001 A | 7/2000 | Burgreen et al. | |
| 6,116,862 A | 9/2000 | Rau et al. | |
| 6,123,659 A | 9/2000 | Blanc et al. | |
| 6,135,710 A | 10/2000 | Araki et al. | |
| 6,146,325 A | 11/2000 | Lewis et al. | |
| 6,149,683 A | 11/2000 | Lancisi et al. | |
| 6,186,665 B1 | 2/2001 | Maher et al. | |
| 6,227,797 B1 | 5/2001 | Watterson et al. | |
| 6,227,820 B1 | 5/2001 | Jarvik | |
| 6,234,772 B1 | 5/2001 | Wampler et al. | |
| 6,254,359 B1 | 7/2001 | Aber | |
| 6,264,635 B1 | 7/2001 | Wampler et al. | |
| 6,278,251 B1 | 8/2001 | Schob | |
| 6,293,901 B1 | 9/2001 | Prem | |
| 6,394,769 B1 | 5/2002 | Bearnson et al. | |
| 6,447,266 B2 | 9/2002 | Antaki et al. | |
| 6,623,475 B1 | 9/2003 | Siess | |
| 6,688,861 B2 | 2/2004 | Wampler | |
| 6,692,318 B2 | 2/2004 | McBride | |
| 6,942,611 B2 | 9/2005 | Siess | |
| 6,991,595 B2 | 1/2006 | Burke et al. | |
| 7,011,620 B1 | 3/2006 | Siess | |
| 7,070,398 B2 | 7/2006 | Olsen et al. | |
| 7,229,258 B2 | 6/2007 | Wood et al. | |
| 7,303,553 B2 | 12/2007 | Ott | |
| 7,338,521 B2 | 3/2008 | Antaki et al. | |
| 7,563,225 B2 | 7/2009 | Sugiura | |
| 7,575,423 B2 | 8/2009 | Wampler | |
| 7,578,782 B2 | 8/2009 | Miles et al. | |
| 7,682,301 B2 | 3/2010 | Wampler et al. | |
| 7,699,586 B2 | 4/2010 | LaRose et al. | |
| 7,699,588 B2 | 4/2010 | Mendler | |
| 7,753,645 B2 | 7/2010 | Wampler et al. | |
| 7,798,952 B2 | 9/2010 | Tansley et al. | |
| 7,802,966 B2 | 9/2010 | Wampler et al. | |
| 7,824,358 B2 | 11/2010 | Cotter et al. | |
| 7,841,976 B2 | 11/2010 | McBride et al. | |
| 7,850,594 B2 | 12/2010 | Sutton et al. | |
| 7,861,582 B2 | 1/2011 | Miyakoshi et al. | |
| 7,862,501 B2 | 1/2011 | Woodard | |
| 7,927,068 B2 | 4/2011 | McBride et al. | |
| 7,959,551 B2 | 6/2011 | Jarvik | |
| 7,963,905 B2 | 6/2011 | Salmonsen et al. | |
| 7,976,271 B2 | 7/2011 | LaRose et al. | |
| 7,988,728 B2 | 8/2011 | Ayre | |
| 7,993,260 B2 | 8/2011 | Bolling | |
| 7,997,854 B2 | 8/2011 | LaRose et al. | |
| 8,002,518 B2 | 8/2011 | Woodard et al. | |
| 8,007,254 B2 | 8/2011 | LaRose et al. | |
| 8,096,935 B2 | 1/2012 | Sutton et al. | |
| 8,118,723 B2 | 2/2012 | Richardson et al. | |
| 8,118,724 B2 | 2/2012 | Wampler et al. | |
| 8,152,493 B2 | 4/2012 | LaRose et al. | |
| 8,152,845 B2 | 4/2012 | Bourque | |
| 8,177,703 B2 | 5/2012 | Smith et al. | |
| 8,282,359 B2 | 10/2012 | Ayre et al. | |
| 8,323,174 B2 | 12/2012 | Jeevanandam et al. | |
| 8,343,028 B2 | 1/2013 | Gregorio et al. | |
| 8,353,686 B2 | 1/2013 | Cook | |
| 8,366,381 B2 | 2/2013 | Woodard et al. | |
| 8,366,599 B2 | 2/2013 | Tansley et al. | |
| 8,376,707 B2 | 2/2013 | McBride et al. | |
| 8,449,444 B2 | 5/2013 | Poirier | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | LaRose et al. | |
| 8,864,643 B2 | 10/2014 | Reichenbach et al. | |
| 9,265,870 B2 | 2/2016 | Reichenbach et al. | |
| 9,533,082 B2 | 1/2017 | Reichenbach et al. | |
| 9,717,832 B2 | 8/2017 | Taskin et al. | |
| 9,717,833 B2 | 8/2017 | Mcbride et al. | |
| 10,029,038 B2 | 7/2018 | Hodges | |
| 10,646,630 B2 | 5/2020 | Hodges | |
| 10,660,998 B2 | 5/2020 | Hodges | |
| 10,857,273 B2 * | 12/2020 | Hodges | A61M 60/818 |
| 2001/0041934 A1 | 11/2001 | Yamazaki et al. | |
| 2002/0147495 A1 | 10/2002 | Petroff | |
| 2002/0149200 A1 | 10/2002 | Fumioka | |
| 2003/0039544 A1 | 2/2003 | Yamazaki | |
| 2003/0068227 A1 | 4/2003 | Yamazaki | |
| 2003/0100816 A1 | 5/2003 | Siess | |
| 2003/0135086 A1 | 7/2003 | Khaw et al. | |
| 2004/0236420 A1 | 11/2004 | Yamane et al. | |
| 2005/0004421 A1 | 1/2005 | Pacella et al. | |
| 2005/0071001 A1 | 3/2005 | Jarvik | |
| 2005/0095151 A1 | 5/2005 | Wampler et al. | |
| 2005/0107657 A1 | 5/2005 | Carrier et al. | |
| 2005/0147512 A1 | 7/2005 | Chen et al. | |
| 2005/0254976 A1 | 11/2005 | Carrier et al. | |
| 2006/0222533 A1 | 10/2006 | Reeves et al. | |
| 2007/0078293 A1 | 4/2007 | Shambaugh, Jr. et al. | |
| 2007/0100196 A1 | 5/2007 | Larose et al. | |
| 2007/0156006 A1 | 7/2007 | Smith et al. | |
| 2008/0021394 A1 | 1/2008 | LaRose et al. | |
| 2008/0269880 A1 | 10/2008 | Jarvik | |
| 2009/0118567 A1 | 5/2009 | Siess | |

(56) References Cited

U.S. PATENT DOCUMENTS

| | | |
|---|---|---|
| 2009/0203957 A1 | 8/2009 | LaRose et al. |
| 2010/0069847 A1 | 3/2010 | LaRose et al. |
| 2010/0145133 A1 | 6/2010 | Bolling et al. |
| 2010/0150749 A1 | 6/2010 | Horvath |
| 2010/0152526 A1 | 6/2010 | Pacella et al. |
| 2011/0054239 A1 | 3/2011 | Sutton et al. |
| 2011/0118998 A1 | 5/2011 | Loose et al. |
| 2011/0144413 A1 | 6/2011 | Foster |
| 2011/0152600 A1 | 6/2011 | Scott et al. |
| 2011/0237863 A1 | 9/2011 | Ricci et al. |
| 2011/0245582 A1 | 10/2011 | Zafirelis et al. |
| 2012/0035411 A1 | 2/2012 | LaRose et al. |
| 2012/0046514 A1 | 2/2012 | Bourque |
| 2012/0095281 A1 | 4/2012 | Reichenbach et al. |
| 2012/0134793 A1 | 5/2012 | Wu et al. |
| 2012/0134832 A1 | 5/2012 | Wu |
| 2012/0172655 A1 | 7/2012 | Campbell et al. |
| 2012/0209057 A1 | 8/2012 | Siess et al. |
| 2012/0253103 A1 | 10/2012 | Robert |
| 2012/0310036 A1 | 12/2012 | Peters et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0261375 A1* | 10/2013 | Callaway .............. A61M 5/168 600/16 |
| 2013/0314047 A1 | 11/2013 | Eagle et al. |
| 2014/0296615 A1 | 10/2014 | Franano |
| 2014/0324165 A1 | 10/2014 | Burke |
| 2015/0005572 A1 | 1/2015 | Reichenbach et al. |
| 2015/0285258 A1 | 10/2015 | Foster |
| 2016/0074574 A1 | 3/2016 | Welsch et al. |
| 2016/0144089 A1 | 5/2016 | Woo et al. |
| 2016/0369814 A1 | 12/2016 | Schibli et al. |

FOREIGN PATENT DOCUMENTS

| | | |
|---|---|---|
| DE | 19854724 | 5/1999 |
| DE | 102009047844 | 3/2011 |
| EP | 150320 | 5/1990 |
| EP | 0583781 | 2/1994 |
| JP | 2009511802 | 3/2009 |
| KR | 20080056754 | 6/2008 |
| WO | 9015640 | 12/1990 |
| WO | 0043054 | 7/2000 |
| WO | 2007040663 | 4/2007 |
| WO | 2008152425 | 12/2008 |
| WO | 2013056131 | 4/2013 |

* cited by examiner

ROTARY SEAL FOR CANTILEVERED ROTOR PUMP AND METHODS FOR AXIAL FLOW BLOOD PUMPING

CROSS-REFERENCES TO RELATED APPLICATIONS

The present application is a Continuation of U.S. patent application Ser. No. 16/317,809 filed Jan. 14, 2019 (Allowed); which is a U.S. National Stage application of PCT/US2017/042858 filed Jul. 19, 2017; which claims the benefit of U.S. Provisional Appln No. 62/365,305 filed Jul. 21, 2016; the disclosures which are incorporated herein by reference in their entirety for all purposes.

This application relates generally to U.S. application Ser. No. 15/216,528 filed Jul. 21, 2016, entitled "Cantilevered Rotor Pump and Methods for Axial Flow Blood Pumping" (now issued as U.S. Pat. No. 10,029,038); U.S. application Ser. No. 14/489,041 filed Sep. 17, 2014, entitled "Pump and Method for Mixed Flow Blood Pumping" (now issued as U.S. Pat. No. 9,533,082); U.S. application Ser. No. 13/273,185 filed Oct. 13, 2011, entitled "Pumping Blood" (now issued as U.S. Pat. No. 9,265,870); all of which are incorporated herein by reference in their entirety for all purposes.

BACKGROUND

This application relates generally to mechanical circulatory support systems, and more specifically relates to improved rotor designs in axial flow blood pumps.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While blood pumps have been effective for many patients, because patients using such devices are living longer, further improvements that prolong the effectiveness and lifetime of such blood pump devices are desired. One challenge frequently encountered in axial blood pumps is the development of thrombus in the bearing assemblies supporting the rotor. Thus, there is a need for improved blood pump designs that avoid thrombus formation over the lifetime of the device.

BRIEF SUMMARY

An axial flow mechanical circulatory support system having an improved rotor design with a sealed bearing assembly that inhibits thrombus formation is provided herein.

In one aspect, the invention provides an improved rotary seal for sealing a bearing assembly in a pump, particularly implantable pumps such as blood pumps. In some embodiments, such pumps include a pump housing defining a blood flow passage, a rotor including a rotatable shaft that extends into the passage such that a distal portion of the rotor facilitates blood flow through the passage upon rotation of the shaft, a mechanical bearing assembly coupled with a proximal portion of the shaft to allow rotation of the rotor during operation of the pump, and a rotary blood seal disposed at an interface of the bearing assembly and the rotatable shaft. The rotary blood seal can include a first face seal disposed on the rotatable rotor shaft and a second face seal disposed on the pump housing or associated component secured thereto. The first and second face seals are adapted to be being slidably engaged to allow rotation of the rotor shaft. In some embodiments, the rotary blood seal is configured with a preload at an interface between the first and second face seals to inhibit any leakage path therebetween to avoid contact between the bearing assembly and any blood flowing through the blood flow passage during operation of the pump.

In some embodiments, the rotary seal is provided in an associated component of the pump housing, such as a rear cover removably coupleable with the pump housing. The first and second face seals of the rotary seal can be formed of silicon carbide, carbon/tungsten, ceramics or any suitable high wear material.

In some embodiments, the rotary blood seal includes a compliance member adapted to provide the preload at the interface between the first and second face seals when the pump is assembled. In one aspect, the compliance member is deflectable in a direction along which the rotor extends. In another aspect, the compliance member is sufficiently rigid to exert a desired biasing force towards the first seal face of the rotor shaft to ensure engagement between the first and second seal faces of the rotary seal.

In some aspects, the preload on the seal is provided by a biasing member or biasing mechanism. The biasing member or mechanism could be defined by a resilient ridge, one or more resilient pins, a coiled spring, one or more resilient spring arms, a slidable shaft, one or more magnets, a piston, or any suitable means. In some embodiments, the biasing member is defined by a combination of elements such as any of those described herein.

In some aspects, the rotary seal is configured such that the preload on the seal is within a suitable range to ensure a robust seal over the lifetime of the device and to withstand a wide range of expected pump operating pressures. In some embodiments, the preload is a predetermined force level or range of forces between 0.5 N and 200 N, a range between 1 N to 100 N, or a range between 20 and 75 N. In some embodiments, the preload is selected or tuned to a desired force level based on the size and/or application of the device having the rotary seal.

In some embodiments, the rotary seal includes first and second sealing faces and a compliance member defined by a ridge or membrane extending from the housing. The compliance member extends at least partly about an opening through which a proximal portion of the rotor shaft extends. The compliance member can be integral with the rear cover or a separate component that is coupled with the housing such as by a laser weld. The compliance member is defined to be deflectable in a proximal direction of the rotor shaft to exert a reaction force in a distal direction along the rotor shaft thereby increasing the sealing contact forces between the first and second seal faces.

In some embodiments, the rotary seal includes first and second sealing faces with a preload provided by one or more magnets. The magnets are configured such that an associated magnetic force during operation of the pump increases a contact force between first and second face seals. Typically, the one or more magnets are permanent magnets. In some embodiments, the magnets includes a first magnet disposed distally of the first face seal along the rotor and a second magnet disposed proximally of the second face seal along the rotor.

In some embodiments, the rotary seal is defined by a pseudo neointima layer that is formed by use of a bioabsorbable material or a sintered, textured surface along the interface between the rotor shaft and pump housing. The pseudo neointimal layer inhibits passage of blood between the first and second face seal and is maintained by the passage of blood through the flow path of the pump device.

In another aspect, methods of pumping that utilize pumps with a rotary seal are provided herein. Such methods include: operating a blood pump to transport blood along a blood flow path through a pump housing of the blood flow pump, and sealing the bearing assembly from any contact with blood flowing along the blood flow path with a radial seal between the bearing assembly and a portion of the rotatable rotor shaft. Operating the blood pump includes rotating a rotatable shaft of the rotor so that movement of the rotor forces blood along the blood flow path, the rotor being rotatably supported by a bearing assembly. Sealing the bearing assembly includes slidably engaging a first face seal disposed on the rotatable rotor shaft with a second face seal disposed on the pump housing or associated component secured thereto, the first and second face seals being slidably engaged to allow rotation of the rotor shaft. The rotary blood seal can be configured with a preload at an interface between the first and second face seals to inhibit any leakage path therebetween thereby avoiding contact between the bearing assembly and any blood flowing through the blood flow passage during operation of the pump.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim. The invention will be better understood upon reading the following description and examining the figures which accompany it.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
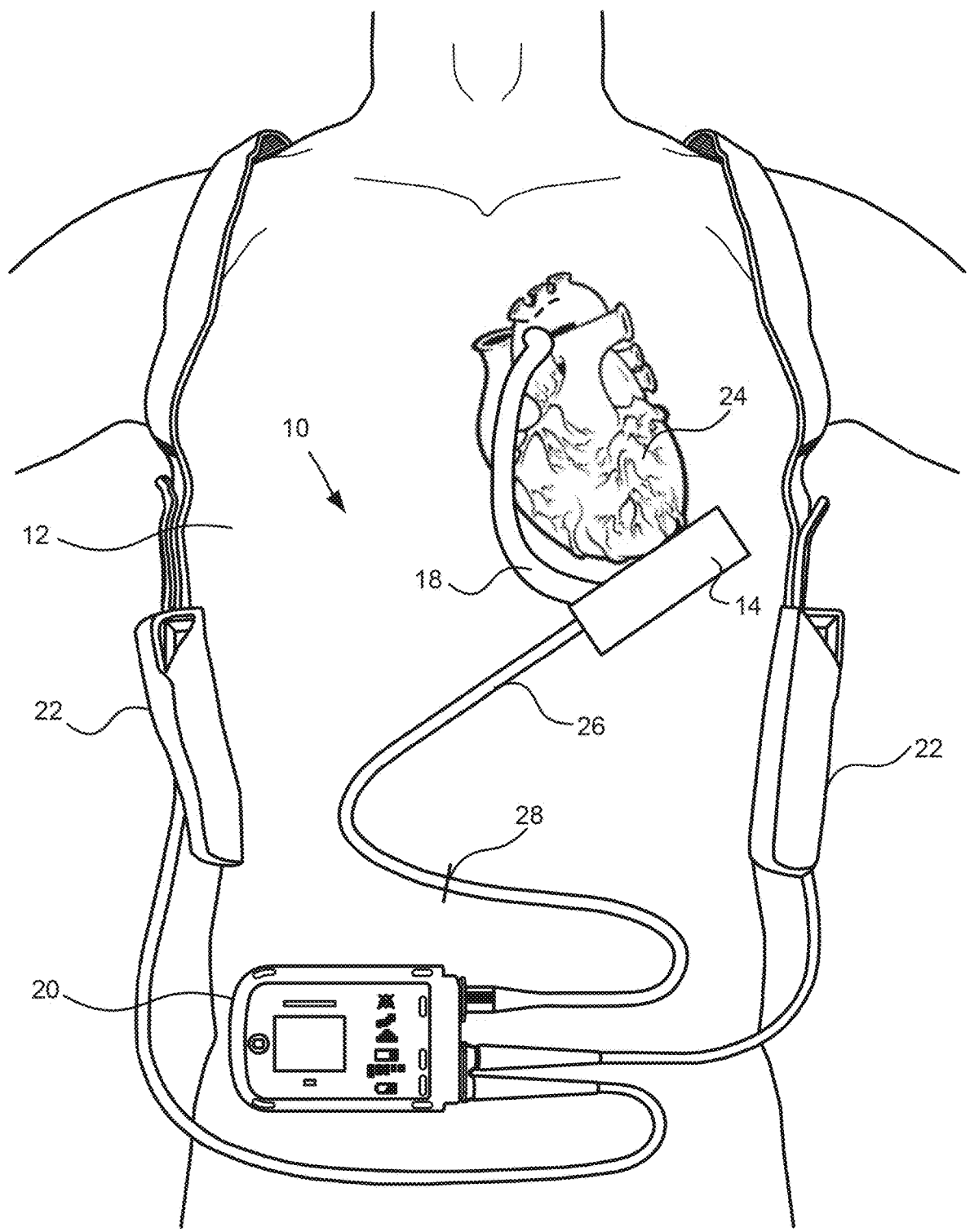
FIG. 1 is an illustration of a mechanical circulatory support system implanted in a patient's body in accordance with embodiments of the invention.

FIG. 1 is an illustration of a mechanical circulatory support system 10 implanted in a patient's body 12. The mechanical circulatory support system 10 include an implantable blood pump 14, outflow cannula 18, system controller 20, and power sources 22. The implantable blood pump 14 may include a VAD that is attached to an apex of the left ventricle, as illustrated, or the right ventricle, or both ventricles of the heart 24. The VAD is typically an axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471; 6,071,093; 6,116,862; 6,186,665; 6,234,772; 6,264,635; 6,688,861; 7,699,586; 7,976,271; 7,997,854; 8,007,254; 8,152,493; 8,652,024; and 8,668,473 and U.S. Patent Publication Nos. 2007/0078293; 2008/0021394; 2009/0203957; 2012/0046514; 2012/0095281; 2013/0096364; 2013/0170970; 2013/0121821; and 2013/0225909; all of which are incorporated herein by reference for all purposes in their entirety. The blood pump 14 may be attached to the heart 24 via a ventricular cuff which is sewn to the heart 24 and coupled to the blood pump 14. The other end of the blood pump 14 connects to the ascending aorta via the outflow cannula 18 so that the VAD effectively diverts blood from the weakened ventricle and propels blood to the aorta for circulation to the rest of the patient's vascular system.

FIG. 1 illustrates mechanical circulatory support system 10 during battery 22 powered operation. A driveline 26 which exits through an exit site 28 in the patient's abdomen, connects the implanted blood pump 14 to the system controller 20, which monitors system 10 operation. Related controller systems applicable to the present invention are described in greater detail below and in U.S. Pat. Nos. 5,888,242; 6,991,595; 8,323,174; 8,449,444; 8,506,471; 8,597,350; and 8,657,733 and U.S. Patent Publication Nos. 2005/0071001 and 2013/0314047; all of which are incorporated herein by reference for all purposes in their entirety. The system may be powered by either one, two, or more batteries 22. It will be appreciated that although the system controller 20 and power source 22 are illustrated outside/ external to the patient body, the driveline 26, system controller 20 and/or power source 22 may be partially or fully implantable within the patient, as separate components or integrated with the blood pump 14. Examples of such modifications are further described in U.S. Pat. No. 8,562, 508 and U.S. Patent Publication No. 2013/0127253, each of which is incorporated herein by reference in its entirety for all purposes.

In some conventional blood pumps, the rotor is suspended by bearing assemblies near opposite ends of the rotor with the rotor blades between. The bearings are disposed within the blood flow path and lubricated, in part, by blood flowing across the bearings. Such bearings are known as bloodwashed bearings.

Figure 2:
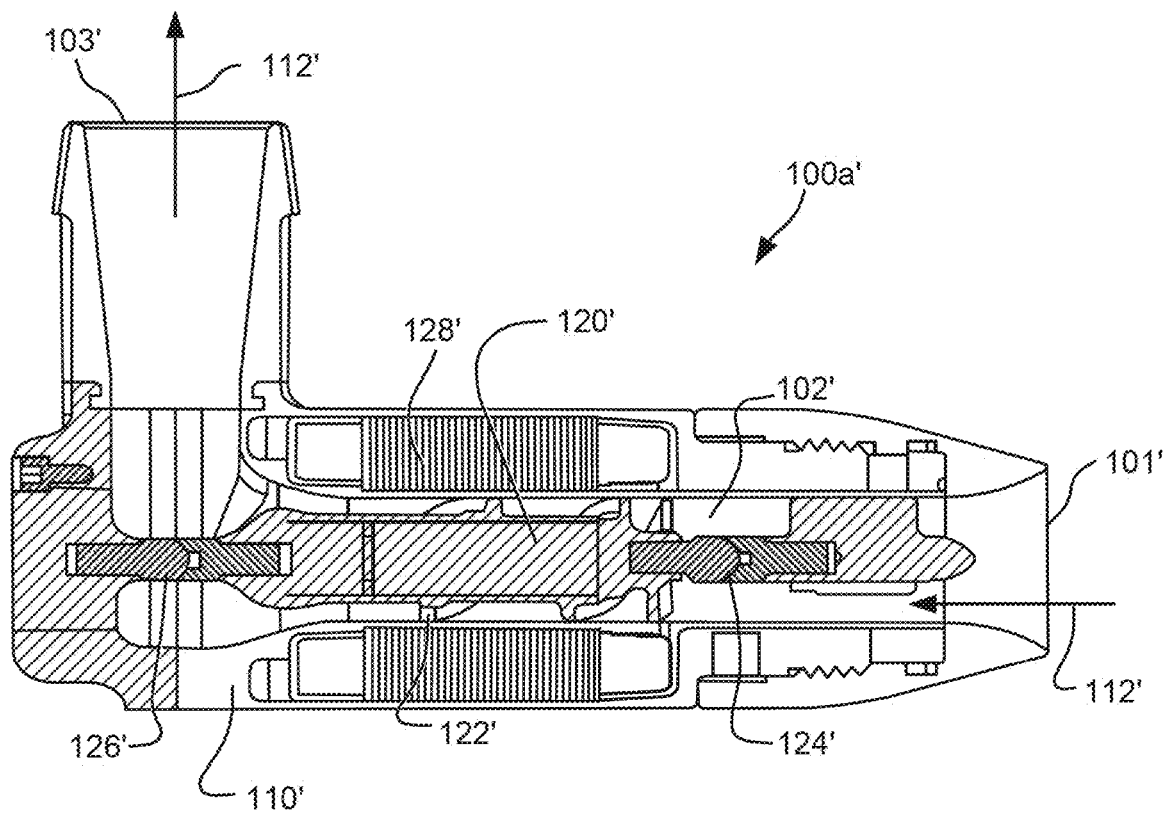
FIG. 2 shows a conventional axial blood flow pump device.

An example of such bearings can be understood by referring to FIG. 2, which shows a conventional axial flow blood pump 100'. The pump includes a housing 110' that defines a blood flow path 112'. Blood enters the housing 110' through an inlet 101', passes through a central tubular region 102' of the housing 110', and exits through an outlet 103'. The housing 110' contains a motor stator 128', which drives rotation of a rotor 120' located in the blood flow path 112'. As the rotor 120' rotates, blades 122' on the rotor 120' impart energy to the blood flow, resulting in pressure and blood flow at the outlet 103'. The rotor 120' is suspended in the housing 110' by fore and aft mechanical, blood-immersed bearings 124', 126' that limit axial translation of the rotor 120'. The bearings 124, 126 also limit the rotor from shifting off its axis of rotation and resist various destabilizing forces that occur during operation.

Studies have revealed that blood-washed bearings tend to develop thrombus over-time at the point of contact between the bearing ball and the cup in which the ball resides. Development of thrombus in the bearings can significantly degrade performance of the pump over time. In twelve chronic in-vivo animal studies, upon completion of the studies, the pumps were explanted and disassembled, after which it was observed that, in 50% of the pumps, either one or both bearings had some level of thrombosis evident.

To address these issues, recent developments include replacing blood washed mechanical bearings in rotary blood pumps that are used to suspend rotors with actively/passively magnetically suspended rotors. This allows for the removal of mechanical bearings in pumps, however, the magnetic levitation of the rotor creates hydrodynamic bearings between the pump housing and rotor. In addition, adding magnetics to VAD's significantly increases the complexity of the design and its operation since the magnets must generally maintain a radial position within the blood flow path as well as a longitudinal position. Due in part to these complexities, current versions of hydrodynamic bearings used in VAD's may still develop thrombus issues.

In one aspect, the invention addresses these challenges associated with conventional designs by reconfiguring the blood pump to include mechanical bearings that are sealed from the blood flow path by a rotary seal. In some embodiments, the mechanical bearing is further excluded from the blood flow path by use of a cantilevered rotor design in which the rotor is supported at one end by a mechanical bearing assembly that remains sealed outside of the blood flow path. The rotary seal can be located between the blood flow path and the bearing assembly. In other embodiments, the bearing assembly can be sealed from blood flow while still maintaining a location within the blood flow path within a cantilevered rotor design or various other rotor designs. In some embodiments, the mechanical bearing assembly is entirely sealed during operation so that there is no need for washing the bearing with blood flow or flushing the assembly with saline. In some embodiments, the rotary seal includes a pair of interfacing face seals attached to the rotor shaft and pump housing or associated component, respectively, such that the face seals maintain a seal between the bearing assembly and the blood flow path while being rotated relative each other. The rotary seal can be maintained by a compliance member that urges one or both face seals to increase sealing contact forces therebetween, a bio-absorbable seal, a silicon carbide id/od bushing seal or any combination thereof.

In some embodiments, the mechanical bearing assembly can include one or more radial bearings at or near one end of the rotor, thereby allowing rotation of the cantilever shaft providing cantilevered support during rotation of the rotor. In some aspects, the radial bearing can be of a metallic (e.g., stainless steel) or non-metallic (e.g., ceramic, polymer) construction. In one aspect, the design allows for the rotor to operate with a single fluid flow path for blood flow through the blood pump, without the need for additional fluid flow paths for saline flushing or waste return. In addition, by reconfiguring the design of the axial flow pump, the bloodwashed mechanical ball and cup bearing design used in conventional axial pump designs can be eliminated. As a byproduct, the inlet stator, front bearing set, and rear bearing set can be removed from the design.

Figure 3:
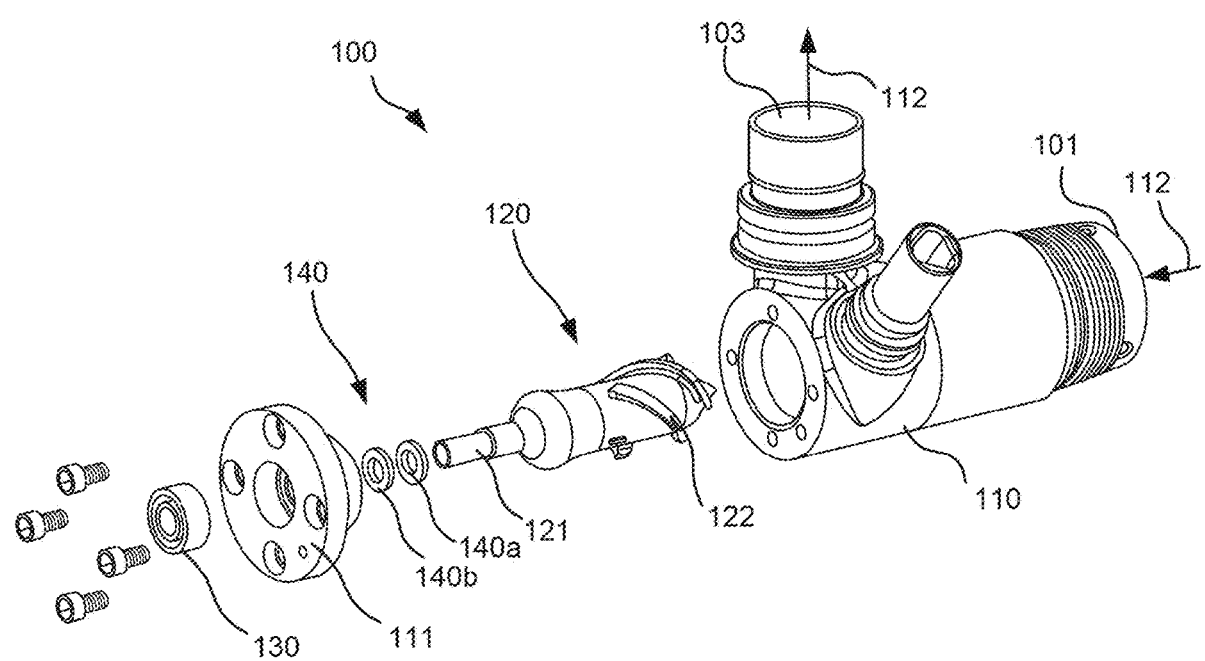
FIG. 3 shows an axial flow blood pump device with an improved rotor design in accordance with some embodiments.

FIG. 3 illustrates an exploded view of an embodiment of an axial blood flow pump design with an improved cantilevered rotor design and rotary seal. The improved axial flow blood pump 100 includes a housing 110 that defines a blood flow path 112 that enters the housing 110 through an inlet 101, passes through a central tubular region of the housing and exits through an outlet 103. Housing 110 may be non-magnetic and may be made of a biocompatible material such as titanium or a suitable ceramic material which is non-thrombogenic, rigid, and exhibits minimum eddy current losses. Housing 110 contains a rotating means, such as a motor stator, adapted to drive rotation of rotor 120. Rotor 120 includes one or more rotor blades 122, typically a group of helical blades, on a distal portion that extends into the blood flow path 112. As rotor 120 rotates, rotor blades 122 impart energy to the blood flow, resulting in pressure and blood flow at the outlet 103. Rotor 120 is suspended in the housing 110 by a mechanical bearing assembly 130 disposed on a proximal portion of rotor 120 that extends through a hole in the rear cover 111 outside the blood flow path.

In some embodiments, rotor 120 is redesigned such that a circular rotor shaft 121 that extends proximally from the rear of the rotor and outside the blood flow path. Such a configuration allows for use of a traditional mechanical bearing (not blood or saline washed). Mechanical bearing 130 can be assembled within the rear cover 111 of the pump housing 110 such that any contact with the blood flow stream is avoided. In this embodiment, the shaft of rotor 120 slides through back cover 111 and can be press fit into the bearing assembly. At the shaft to plug interface, a mechanical rotary seal 140 can be used to further ensure blood contact is avoided. A design of this nature reduces the static to dynamic interfaces from two to one. Furthermore, unlike blood washed bearings, this design does not rely on blood as a lubricant. Rotary seal 140 keeps the blood from being used as a lubricant, which allows blood to be eliminated as a lubricant within rotary type blood pump devices. Since a sealed mechanical bearing assembly is used, this allows for a bearing design that utilizes various other types of lubricant (e.g., oil-based, silicone) and could use and/or adapt common bearings and lubricants from the mechanical arts as would be understood by one of skill from the description herein. Such mechanical bearings may provide improved performance and durability and increased life-times as compared to saline purged or blood washed designs.

Figure 4:
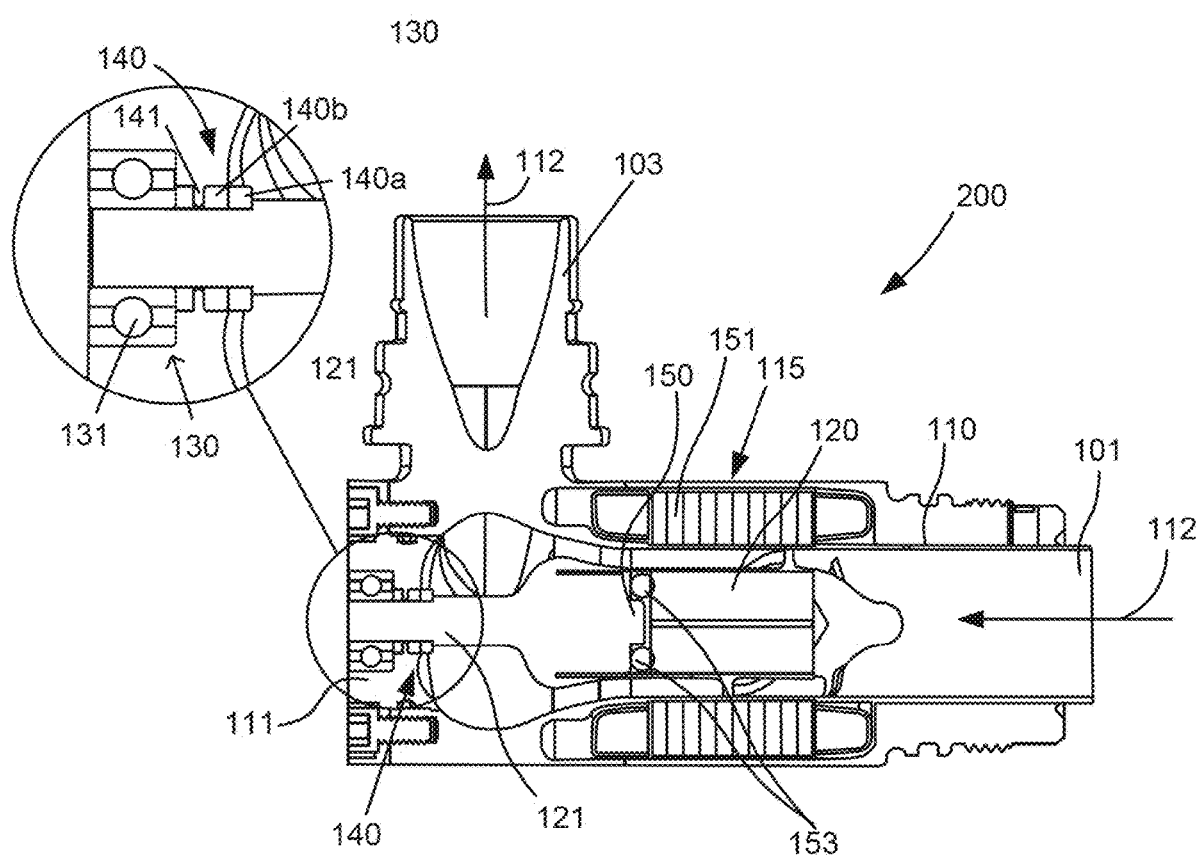
FIG. 4 shows another axial flow blood pump device with an improved rotor design in accordance with some embodiments.

Since mechanical bearings 130 couple the rotor at only one end, it provides cantilevered support and withstands lateral deflection of the rotor by applying a torque through the proximal portion. In some embodiments, the mechanical bearing may be selected to have an axial thickness extending along an axis of the rotor shaft between 0.050" to 0.500" to allow the bearing to withstand greater deflecting forces and apply greater reactive torques. In some embodiments, the device may include a mechanical bearing 130 consisting of multiple stacked radial bearing, such as two stacked radial bearings, as shown in FIG. 4. In another aspect, rotor 120 includes a fluid-tight seal 140 disposed between a proximal portion of the rotor coupled with mechanical bearing assembly 130 and a distal portion from which the rotor blades extend within the blood flow path.

As shown in FIG. 3, the rotary seal 140 includes two interfacing components, first seal face component 140a that is secured to the rotor shaft and revolves with the shaft and second seal face component 140b that remains secured with rear cover 111. Each of seal face is circular in shape with a central opening through which the rotor shaft extends and includes a flat surface that engages against a corresponding flat surface of the other seal face to provide a fluid-tight seal and inhibit blood flow into the bearing assembly while allowing rotation of the rotor shaft within the bearing assembly. One or both of the first and second components 140a, 140b can be formed of a hard and/or rigid material, such as silicon carbide, carbon/tungsten, ceramic, or any alloy or material suitable for withstanding the heat and variable forces that may occur during operation and maintaining a fluid-tight seal over the lifetime of the device. Also, one or both of the seals can be configured with a preload to allow the seals to track on one another while maintaining a sufficient seal. Examples of such rotary seal configurations are detailed further below.

In one aspect, the invention provides a methods of creating a fluid tight rotary mechanical seal between the dynamically spinning rotor shaft and the static rear cover of an axial flow cantilevered pump design. Advantageously, the described rotary seals prevent or inhibit blood from making contact with a mechanical bearing, non-blood washed, in the rear cover. In some embodiments, this seal consists of two circular face seals made of a high wear material such as silicon carbide, ceramics, or other like materials. One half of the seal is attached to the spinning rotor shaft and the other is attached to the static rear cover. Upon assembly of the system, the two faces seals are brought into intimate contact with each other. In some embodiments, a slight preload is provided at the seal interface in order to ensure there is no leak path. In order to achieve a preloading of these seals, a compliance member or mechanism can be included. One source of this compliance can be from a precision machined membrane in the rear cover. The static portion of the seal can be attached to this compliant membrane. When the other half of the seal is assembled, the seal presses against this compliant membrane causing the membrane to deflect. The deflection caused by assembly will impart a known reaction force against the mating rotary seal. Such compliant members or membranes can be defined within the aft or rear housing or can be laser welded thereto. Laser welding allows more design freedom around shapes, attachments, and force/deflection characteristics.

Such a configuration allows for the use of a mechanical, non-blood washed, bearing to be used to suspend the rotor in an axial flow cantilevered rotor pump design. Such rotary seals ensure that the bearing stays isolated and free from contaminates and formation of thrombus associated with blood flow. One advantage of the rotary seal configurations described herein, is that a barrier is created between the blood flow path in the pump and other critical components (e.g., bearings, sensors) that cannot interface with blood.

In another aspect, improved sealing between the two halves of the rotary seal can be facilitated by the use of magnets. Such magnets can be integrated into each half of the seal assembly. As the seals are brought together, the magnetic force from each half attract each other which would provide a magnetically coupled preload allowing the seal to operate in a liquid tight manner. Use of magnets in this manner can eliminate the need for a compliant membrane.

In yet another aspect, improved sealing within a rotary seal can be provided by a precision fitment between the shaft (od; outside diameter) and the housing (id; inside diameter) defined to prevent passage of blood. This approach can greatly simplify the rotary seal yet still create a robust enough of a barrier to prevent passage of blood or blood moisture vapors into a bearing assembly of the pump.

Another way to create a rotary blood seal is through the use of an id/od bushing seal. This approach uses a precision manufactured silicon carbide shaft on the outside diameter (od) that marries with a precision manufactured silicon carbide disc with a through hole, which is the inside diameter (id). This can greatly simplify the seal since no compliance is required.

In still yet another aspect, improved sealing within a rotary seal of an implantable device can be provided by use of biologics to create a long term seal. In such embodiments, titanium sintered surfaces can be used to create a pseudo neointima layer that interface well with blood. Use of sintered surfaces within an area around the rotating shaft promotes formation of a pseudo neointima area. This pseudo neointima area can also be initiated through a bio absorbable material. The pseudo neointima plugs the gap around the spinning shaft and stationary rear cover creating a seal.

It is appreciated that the rotary seals described herein are not limited to axial flow pumps, or even blood pumps, and could be used in various implantable or non-implantable pump devices, or any field there is a need for a robust mechanical rotary seal that is liquid tight and has minimal wear over a long period of time.

Examples of such rotary seals that are suitable for use in a cantilevered rotor design are described in the following figures.

FIG. 4 shows another exemplary pump 200 having a cantilevered rotor 120 in which the supporting mechanical bearing 130 is disposed outside the blood flow path and rotary seal 140 disposed between the blood flow path and bearing assembly 130. In this embodiment, rotary seal 140 includes two interfacing seals, rotating face seal 140a attached to rotor shaft 121 to rotate with the shaft and fixed face seal 140b attached to the rear cover 111 of pump housing 110. Each face seal interfaces with each other along a flat, precision polished surface to form a seal that prevents passage of any blood flow therebetween. Each face seal can be integral with the component with which it is attached, or more typically, is a separate component formed of a high wear material that is secured to the corresponding component. Typically, rotary seal 140 is preloaded such that there is a minimum contact force between face seals 140a, 140b to ensure a suitable sealing between interfacing surfaces for use with the variable pressure and flowrates within the blood flow passage of the pump. In this embodiment, the preload force is provided by a compliance member 141 that exerts a force when the pump is assembled to increase contact forces between seal faces. Here, compliance member 141 is defined as a thin wall, ridge or membrane that extends inwardly towards the rotor shaft. The fixed face seal is disposed against the compliance member such that compliance member 141 presses fixed face seal 140b against rotating face seal 140a during operation of the pump. It is appreciated that the dimensions and material properties of compliance member 141 can be defined to provide a desired preload in order to provide a suitable sealing contact force between seal faces as needed for a particular application. In some embodiments, compliance member 141 can be formed from rear cover 111 of pump housing, such as by precision machining.

In this embodiment, mechanical bearing assembly 130 includes two radial bearings stacked on the proximal portion of the rotor 120. Rotor 120 includes permanent drive magnets 150 to facilitate being rotationally driven by a motor stator 151 having electrically conductive coils. The coils are placed within an enclosure which surrounds the blood flow path and the rotor 120 disposed within pump housing 110. The motor stator 151 serves to rotate rotor 120 by the conventional application of electric power to the coils to drive the permanent drive magnets 150 incorporated into rotor 120. Elastomeric O-rings 153 keep the magnets from rotating in the rotor. Such magnets are selected for magnetic properties, length, and cross-sectional area in order to provide good electromagnetic coupling with the magnetic forces created by the motor stator 151. In some embodiments, the motor is a three phase, brushless DC motor. In other embodiments, the motor can be a toroidal, three phase or wye connected design. The stator may have a back iron design which is consistent with a typical radial flux gap motor. If desired, motor stator 151 can be incorporated within a separate, hermetically sealed enclosure that slides over pump housing into position. In some embodiments, the body of rotor 120 includes a magnetically hard ferromagnetic material, i.e., a material which forms a strong permanent magnet and which is resistant to demagnetization. The material of rotor body 120 is typically selected to be biocompatible and substantially non-thrombogenic. Rotor 120 can be formed as a unitary component or can be formed of separate components joined together. In some embodiments, the rotor body is formed as a unitary mass of a suitable material, such as an alloy of platinum, titanium, and cobalt. In other embodiments, the rotor body may be formed from a magnetic metal such as an iron-nickel alloy with an exterior coating of another material to increase the body's biocompatibility. Further details regarding suitable rotor designs are described in U.S. Pat. Nos. 5,588,812; 62/084,946; 2016/0144089; 2014/0324165; and U.S. Pat. No. 9,265,870; each of which is incorporated herein by reference in its entirely for all purposes.

Figure 5:
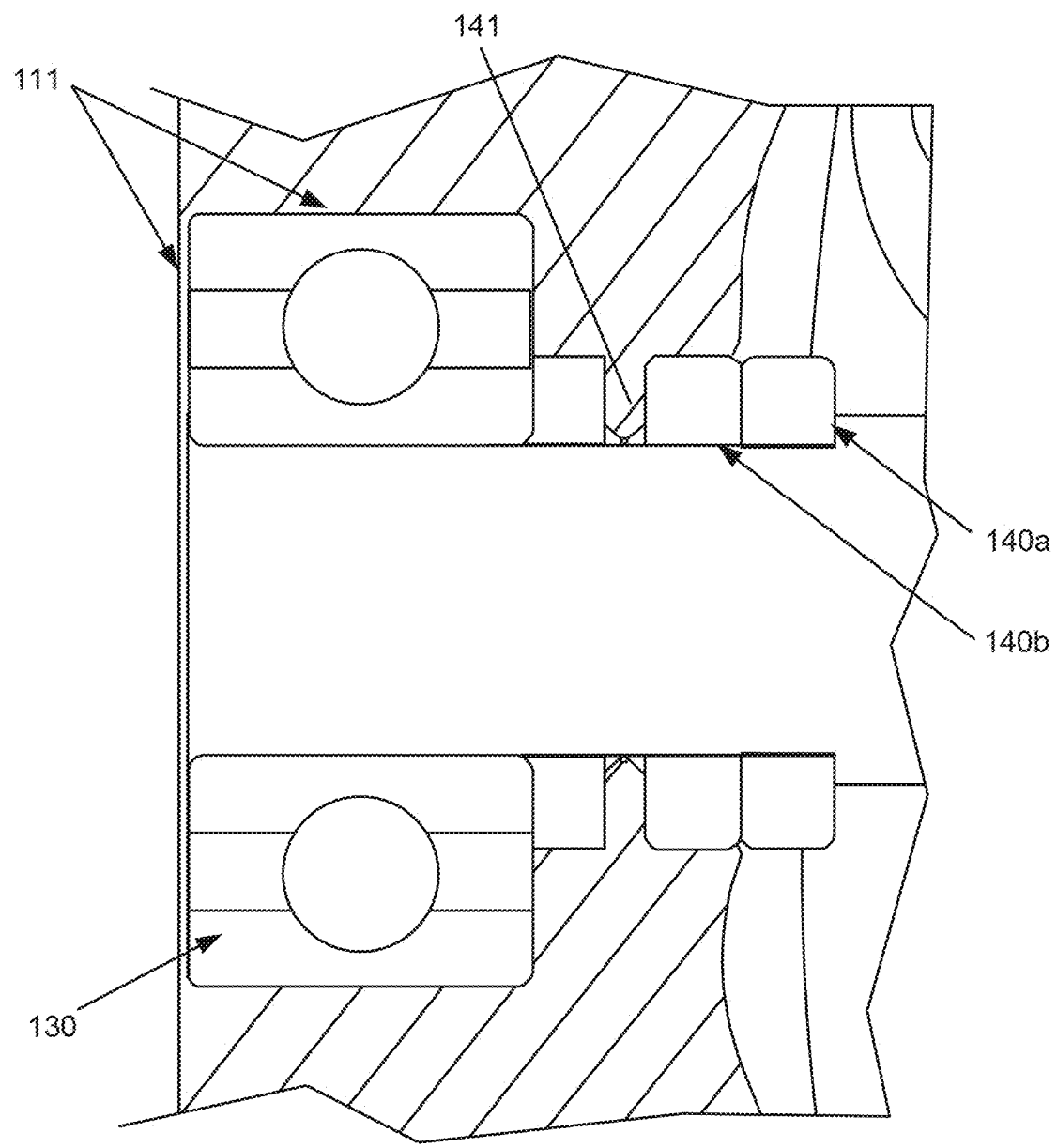
FIG. 5 shows a detailed view of a rotary seal for use with a cantilevered rotor in accordance with some embodiments.

FIG. 5 shows a detail cross-sectional view of rotary seal 140 of FIG. 4. As can be seen, compliance member 141 extends from rear cover 111 in which bearing assembly 130 is secured. Compliance member 141 can be deflectable such that, when the pump is assembled, compliance member 141 is in a deflected state that exerts a desired force against interfacing face seals. In some embodiments, compliance member is defined to angle in a distal direction along the rotor shaft such that when assembled within the pump, compliance member extends substantially perpendicular to the rotor shaft, as shown in FIG. 5. Typically, compliance member extends around the hole in rear cover 111 through which rotor shaft 121 extends to provide a uniform and continuous force about the rotary seal 140. This further reduces uneven wear and tear which improves the useful life of the seal.

Figure 6A:
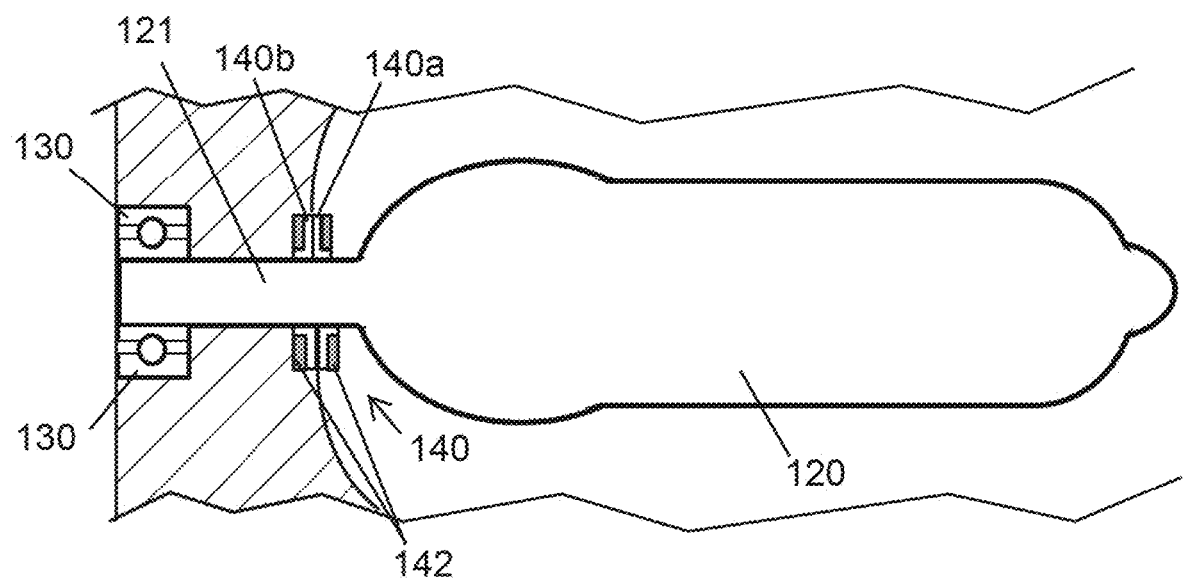
FIGS. 6A-6B show a cantilever rotor design supported by a bearing assembly and having a rotary seal in accordance with some embodiments.
Figure 6B:
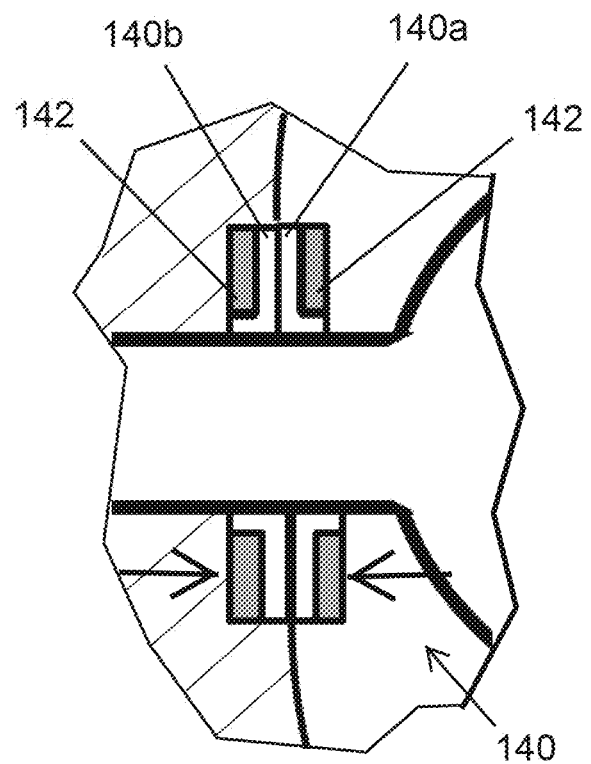

FIG. 6A show another embodiment of a cantilever rotor configuration having a preloaded rotary seal 140. In this embodiment, the preload is provided by a pair of magnets 142 disposed outside the interfacing face seals 140a, 140b, as shown in the detail view of FIG. 6B. Typically, magnets 142 are circular and dimensioned to extend along an outer side of each face seal, thereby providing a uniform preload force that increases the sealing contact forces between seal faces 140a, 140b (see arrows). In this embodiment, magnets 142 are permanent magnets, although some embodiments and applications, such magnets could include one or more electromagnets. Magnets 142 can be selected and sized in order to fine-tune the resulting preload force. Use of permanent magnets is desirable in many implantable applications as this does not increase the power requirements of the implantable device.

Figure 7:
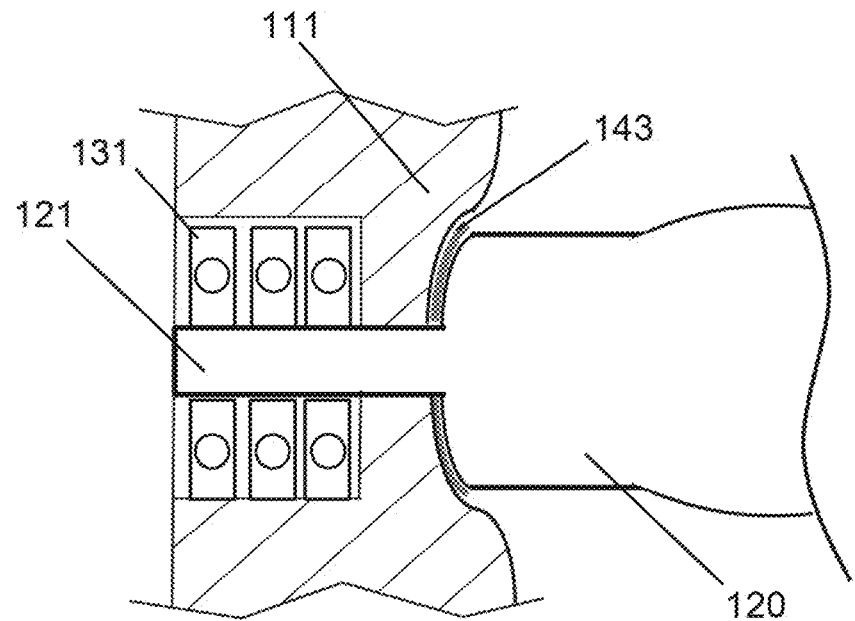
FIGS. 7 and 8 shows alternative cantilever rotor designs supported by a bearing assembly and having a rotary seal in accordance with some embodiments.
Figure 8:
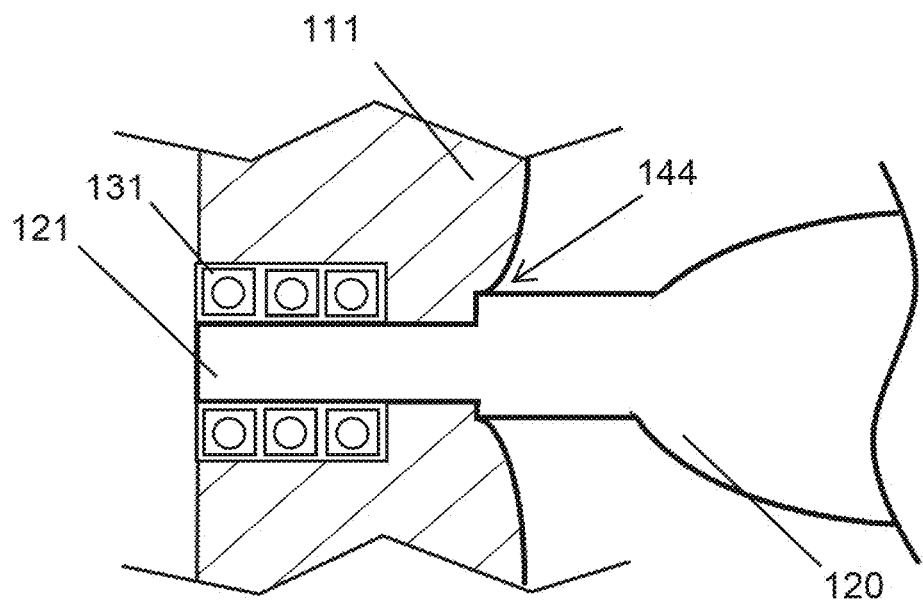

FIGS. 7-8 illustrate alternative embodiments of a rotary seal which include features that can be used in the alternative or in addition to the features described above. FIG. 7 shows another embodiment in which the show another embodiment of a cantilever rotor 120 configuration having a rotary seal that includes a bio-absorbable material 143 that fills the interface between rotor shaft 121 and a portion of rear cover 111 to prevent leakage of blood from the blood flow path to bearing assembly 131. FIG. 8 illustrates another embodiment where rotary seal relies on a tight fitment 144 between rotor shaft 121 and a portion of rear cover 111 or pump housing to prevent flow of blood to bearing assembly 130. Tight fitment 144 can be defined between a curved portion or a shoulder region of rear cover 111 or pump housing that substantially conforms with a corresponding feature in rotor shaft 121. The rotary seal can utilize similar interfacing flat surfaces as the seal faces described above or can rely on interfacing surface of corresponding contours. In one aspect, this approach may rely on formation of thrombus along the interface, which prevents flow blood beyond the interface into the bearing assembly.

Figure 9:
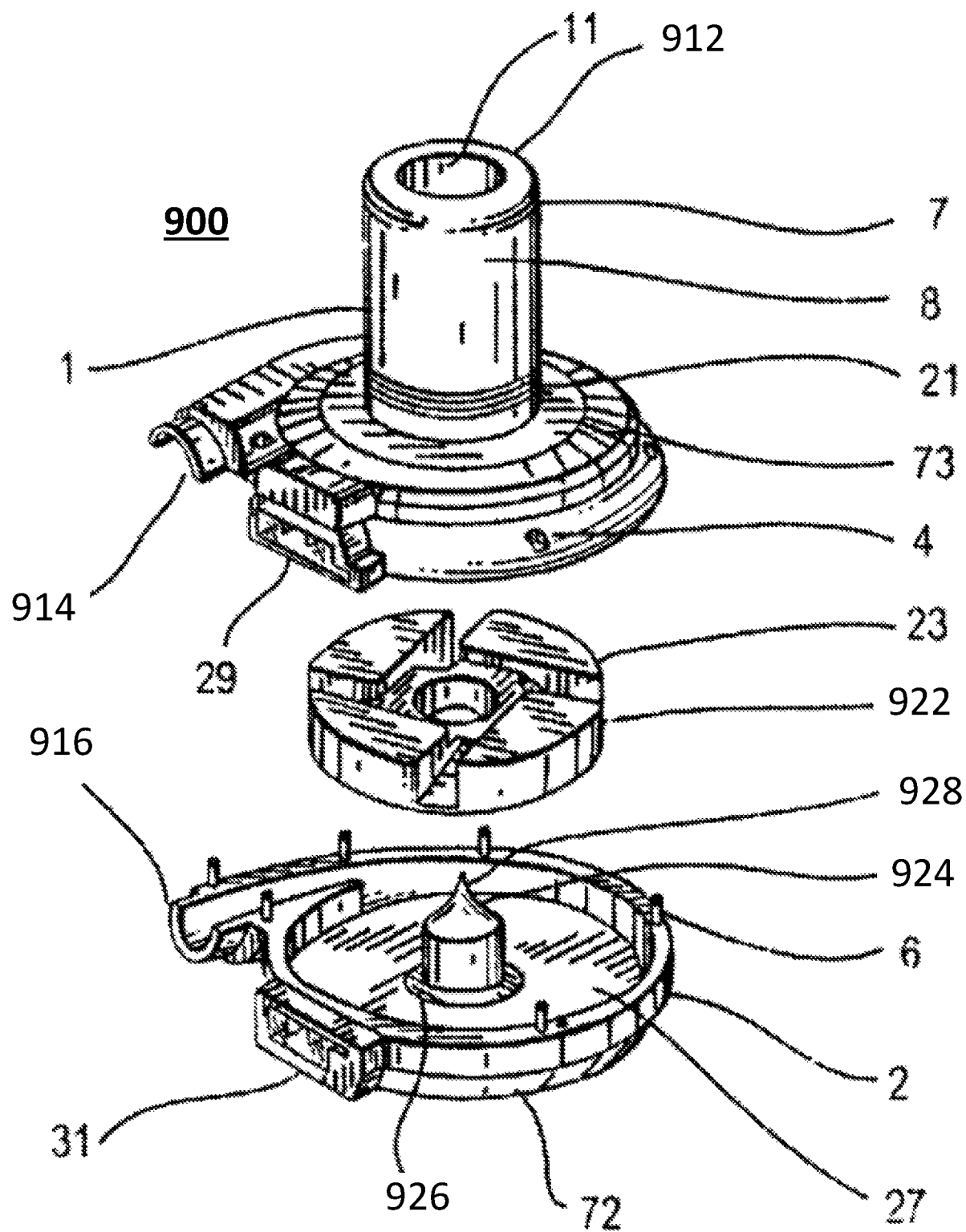
FIG. 9 is an exploded view of a centrifugal rotary blood pump.

Referring now to FIG. 9 there is shown a centrifugal rotary blood pump 900 having a pump housing that consists of a substantially circular front or upper pump casing 1 and a substantially circular rear or lower pump casing 2 of equal diameter that interlocks with the upper pump casing 1 to form a closed pumping chamber between them. The configuration of the upper and lower pump casings is such that the assembled pump housing defines a substantially cylindrical pumping chamber therein. In one embodiment the pumping chamber has a displaced volume of 45 cc. The upper pump casing 1 may have a plurality of peripheral positioning holes 4 for receiving a corresponding plurality of positioning pins 6 projecting from the periphery of the lower pump casing 2. The configuration of positioning holes 4 and positioning pins 6 ensures that the upper pump casing 1 and the lower pump casing 2 interlock in the correct position when the rotary blood pump 900 is assembled. The contact area between the upper pump casing 1 and the lower pump casing 2 may be sealed, for example using screws or a chemical sealant.

In the embodiment shown in FIG. 9 blood is supplied to the pump through an axial inlet cannula 7 adapted for apical insertion into a heart ventricle. The cannula 7 is affixed to or may be integral with the upper pump casing and is in fluid flow communication with the pumping chamber 3 of the pump 900. An embodiment of the inflow cannula 7 is of two-piece design, consisting of an outer cylindrical section 8 and a coaxial inner cylindrical section. The outer cylindrical section 8 of the inflow cannula 7 may be welded in an appropriate sealable manner to the outer surface of the upper pump casing 1. The inner cylindrical section defines an inlet channel 11 for the blood when the pump is installed and in operation. The sections may be laser welded together at the outer end 912 of the cannula, shown in FIG. 9. In one embodiment, the outside diameter of the outer section 8 is about 0.81 inches while the inside diameter of the inner section is about 0.50 inches.

In one embodiment, the pumping chamber is in fluid-flow communication with a volute or diffuser section to avoid alteration of the position of the impeller in a radial direction as blood pressure increases during operation of the pump. The upper pump casing 1 and lower pump casing 2 together define the diffuser by a pair of complementary upper and lower half-round sections 914 and 916 formed as part of the upper and lower housing casings, respectively. The sections 914 and 916 together define a short open-ended cylindrical diffuser tube. The diffuser extends completely around the circumference of the pump terminating at a tangential outlet port. In one embodiment, the cross section of the diffuser section enlarges from an inlet end along its length to a maximum at the outlet. Blood exits the pumping chamber through the outlet in a direction substantially perpendicular to the longitudinal axis of the inlet cannula 7, an arrangement that has been found to be anatomically advantageous for locating the pump in the pericardial space. When the pump is installed and in operation, the outlet is adapted to be joined to an outflow graft, which in turn is suitably connected to the aorta. In one embodiment, the pump housings or casings and the cannula may be made of titanium, a biocompatible titanium alloy, or a biocompatible ceramic material. The pump structure may be machined from titanium or an alloy thereof. Alternatively, the pump structure, including the cannula, may be formed entirely from ceramic material.

With reference to FIG. 9, a motor rotor or pump impeller 922 is located within the pumping chamber between the upper pump casing 1 and the lower pump casing 2. The impeller 922 is circular in cross section and may have a diameter of an inch or an inch and a quarter. The impeller is provided with a central hole 23. A center post or spindle 924 is attached to the lower pump casing 2 and protrudes from the axial center thereof through the impeller hole 23 when the pump is assembled to support rotation of the impeller in the manner described in detail below. The center post 924 is provided with a peripheral lower flange 926 by which a lower annular ceramic disc 27 is retained to an interior surface of the lower pump casing 2. In one embodiment, the gap between the outer diameter of the center post 924 and the diameter of the impeller hole 23 is in the range of from 0.019 inches to 0.029 inches. The top portion of the center post 924 is formed as a conical surface 928. A substantial portion of the conical surface 928 of the center post protrudes above the impeller hole 23 during operation of the pump. In one embodiment, the radius of curvature of the cone shape is a relatively constant 0.389 inches. The tip of the cone is not necessarily a sharp point having, in one embodiment, a blending radius of 0.0900 inches.

In operation, blood entering the cannula 7 from a heart ventricle passes axially over the conical surface of the center post 924 into the pumping chamber where it is engaged by the rotating impeller. Blood entering the pumping chamber from the cannula 7 is redirected from axial flow exiting the cannula to a radial flow within which the impeller 922 is submerged. The rotating impeller presses the blood radially into a whirling motion as a result of the configuration of the spinning impeller, described in detail below, and moves within the diffuser at the perimeter of the pumping chamber to the outlet.

Figure 10:
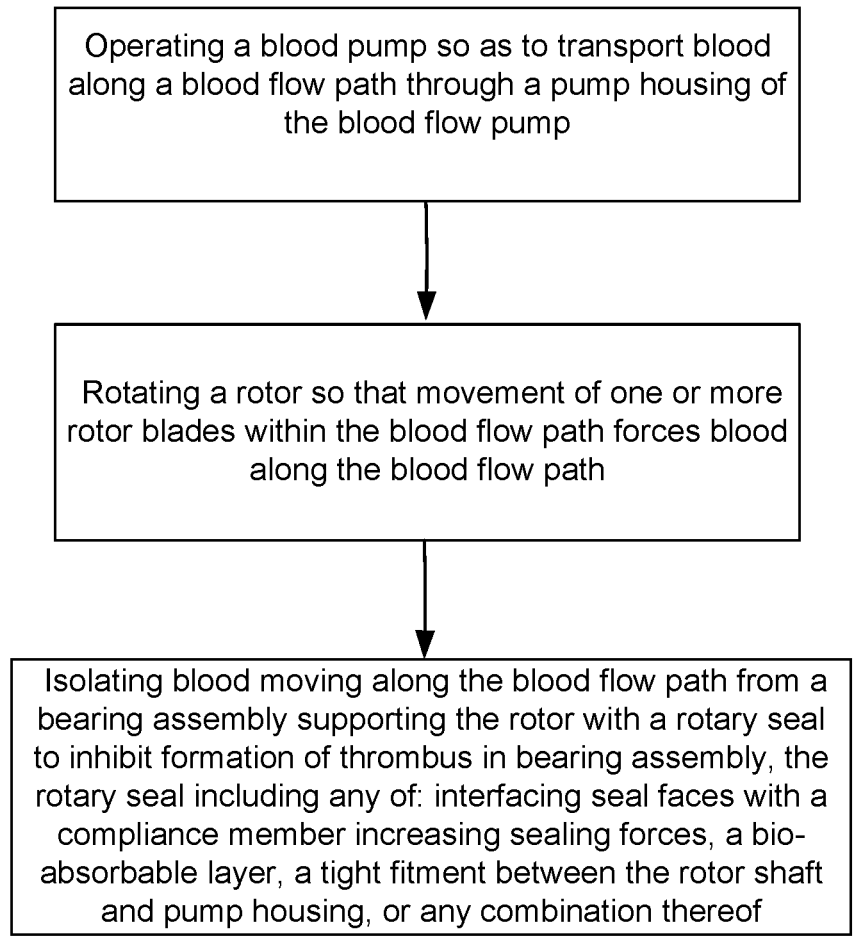
FIG. 10 shows methods of pumping blood with a blood pump in accordance with some embodiments.

FIG. 10 depicts a method of pumping blood with a blood pump that includes: operating a blood pump to transport blood along a blood flow path through a pump housing of the blood flow pump. Operation of the pump can be performed by rotating a rotor of the pump so that movement of one or more rotor blades within the blood flow path forces blood along the blood flow path. The method further includes: sealing a bearing assembly supporting the rotor from blood flowing through the pump so as to inhibit formation of thrombus in bearing assembly. The rotary seal can include any of interfacing seal faces with a compliance member increasing sealing forces, a bio-absorbable layer, a tight fitment between the rotor shaft and pump housing, or any combination thereof.

While the above embodiments depict axial flow pump device, it is appreciated that the cantilever rotor design may be utilized in various other rotary type blood pumps in accordance with the aspects described herein. In addition, the radial seals may be applied to various other embodiments to isolate various other bearing assembly designs from the blood flow path as desired. It is further appreciated that there are any number of mechanical bearing options that can be integrated within the designs described herein. For example, some embodiments may utilize integral duplex bearings and preloaded bearings that have increased precision. There are also many different types of bearing lubrication options available as well as rotary shaft seals that may be incorporated into various embodiments.

In alternative embodiments, aspects of the invention described above may be used in centrifugal pumps. In centrifugal pumps, the rotors are shaped to accelerate the blood circumferentially and thereby cause blood to move toward the outer rim of the pump, whereas in the axial flow pumps, the rotors are more or less cylindrical with blades that are helical, causing the blood to be accelerated in the direction of the rotor's axis.

In the foregoing specification, the invention is described with reference to specific embodiments thereof, but those skilled in the art will recognize that the invention is not limited thereto. Various features and aspects of the above-described invention can be used individually or jointly. It is appreciated that any of the aspects or features of the embodiments described herein could be modified, combined or incorporated into any of the embodiments described herein, as well as in various other types and configurations of pumps. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable blood pump comprising:
   a pump housing defining a blood flow passage therethrough;

a rotor including a rotatable shaft that extends into the blood flow passage;

a mechanical bearing assembly coupled with a first portion of the rotatable shaft so as to allow rotation of the rotor during operation of the pump; and a rotary blood seal assembly disposed at an interface of a first portion of the pump housing and the rotatable shaft so as to avoid contact between the bearing assembly and blood flowing through the blood flow passage during operation of the pump, wherein the rotary blood seal assembly comprises a first face seal component disposed on the rotatable rotor shaft and a second face seal component disposed on the first portion of the pump housing, and wherein the rotary blood seal assembly is configured with a preload to urge the first seal component and the second face seal component against each other to inhibit leakage, wherein the preload is provided at least in part by a first magnet disposed along the first face seal component and a second magnet disposed along the second face seal component, the first and second magnets being configured such that an associated magnetic force between the first and second magnets during the operation of the pump increases a contact force between the first and second face seal components.

2. The blood pump of claim 1, wherein the first portion of the pump housing is a rear cover removably coupleable with a second portion of the pump housing.

3. The blood pump of claim 1, wherein the first and second face seal components comprise silicon carbide, ceramics, or any suitable high wear material.

4. The blood pump of claim 1, wherein the first and second face seal components are slidably engaged with each other.

5. The blood pump of claim 4, wherein the rotary blood seal assembly further includes a compliance member adapted to provide another part of the preload at the interface between the first and second face seal components when the pump is assembled.

6. The blood pump of claim 5, wherein the compliance member is deflectable in a direction along which the rotor extends.

7. The blood pump of claim 5, wherein the compliance member is sufficiently rigid to exert a desired biasing force towards the first face seal component of the rotatable rotor shaft so as to ensure engagement between the first and second face seal components of the rotary blood seal assembly.

8. The blood pump of claim 5, further comprising a rear cover of the pump housing, wherein the compliance member is a ridge or membrane extending from the rear cover of the pump housing that extends at least partly about an opening through which the first portion of the rotatable rotor shaft extends.

9. The blood pump of claim 8, wherein the ridge or membrane is integral with the rear cover and deflectable so as to exert a biasing force along the rotatable rotor shaft.

10. The blood pump of claim 1, wherein the rotary blood seal assembly further includes a bio-absorbable seal to inhibit intrusion of blood between the first and second face seal components.

11. The blood pump of claim 1, wherein at least one of the first and second magnets includes a permanent magnet.

12. The blood pump of claim 1, wherein the first magnet is disposed along an end portion of the first face seal component toward an interior of the pump housing.

13. The blood pump of claim 12, wherein the second magnet is disposed along an end portion of the second face seal component toward an exterior of the pump housing.

14. The blood pump of claim 12, wherein the blood pump is an axial flow pump.

15. The blood pump of claim 12, wherein the blood pump is a centrifugal pump.

16. A rotary blood seal assembly for a blood pump comprising:

a first face seal component configured to be disposed on a rotatable rotor shaft of the blood pump; and a second face seal component configured to be disposed on a portion of a housing of the blood pump, wherein the rotary blood seal assembly is configured to be disposed at an interface of the portion of the pump housing and the rotatable shaft; and wherein the rotary blood seal assembly is configured with a preload to urge the first seal component and the second face seal component against each other to inhibit leakage, wherein the preload is provided at least in part by a first magnet disposed along the first face seal component and a second magnet disposed along the second face seal component, the first and second magnets being configured such that an associated magnetic force between the first and second magnets during the operation of the blood pump increases a contact force between the first and second face seal components.

17. The blood pump of claim 16, wherein the first and second face seal components are slidably engaged with each other.

18. The blood pump of claim 17, wherein the rotary blood seal assembly further includes a compliance member adapted to provide another part of the preload at the interface between the first and second face seal components when the pump is assembled.

19. The blood pump of claim 18, further comprising a rear cover of the pump housing, wherein the compliance member is a ridge or membrane extending from the rear cover of the pump housing that is configured to extend at least partly about an opening through which a portion of the rotatable rotor shaft extends.

* * * * *